United States Patent
Totoki

(10) Patent No.: US 9,429,505 B2
(45) Date of Patent: Aug. 30, 2016

(54) PARTICLE SIZE DISTRIBUTION MEASURING APPARATUS

(71) Applicant: SHIMADZU CORPORATION, Kyoto, Kyoto (JP)

(72) Inventor: Shinichiro Totoki, Kyoto (JP)

(73) Assignee: SHIMADZU CORPORATION, Kyoto-shi (JP)

(*) Notice: Subject to any disclaimer, the term of this patent is extended or adjusted under 35 U.S.C. 154(b) by 28 days.

(21) Appl. No.: 14/573,032

(22) Filed: Dec. 17, 2014

(65) Prior Publication Data
US 2016/0178500 A1    Jun. 23, 2016

(51) Int. Cl.
G01N 15/02    (2006.01)
G01N 15/14    (2006.01)

(52) U.S. Cl.
CPC ....... *G01N 15/0205* (2013.01); *G01N 15/0211* (2013.01); *G01N 15/1434* (2013.01); *G01N 2015/1493* (2013.01)

(58) Field of Classification Search
None
See application file for complete search history.

(56) References Cited

U.S. PATENT DOCUMENTS 6,833,918 B2 * 12/2004 Kurozumi .......... G01N 15/0211
356/336

FOREIGN PATENT DOCUMENTS

| JP | 11-83721 A | 3/1999 |
|----|------------|--------|
| JP | 11-083722 A | 3/1999 |
| JP | 2000-304679 A | 11/2000 |
| JP | 2002-116133 A | 4/2002 |
| JP | 2007-170841 A | 7/2007 |

OTHER PUBLICATIONS

Office Action dated Jul. 28, 2015, issued in counterpart Japanese application No. 2012-172021 (3 pages).
Office Action dated Dec. 15, 2015, issued in counterpart Japanese Patent Application No. 2012-172021 (3 pages).

* cited by examiner

*Primary Examiner* — Kara E Geisel
*Assistant Examiner* — Amanda Merlino
(74) *Attorney, Agent, or Firm* — Westerman, Hattori, Daniels & Adrian, LLP

(57) ABSTRACT

In order for a parallel light beam to enable formation of an image at the center of a photodetector 52 without the use of an actuator for the adjustment by an order of micrometers, a particle size distribution measuring apparatus 1 is provided with: a control unit 70 for calculating the distribution of particle size; a lens 21, 22 which is located between a light source unit 40 and a cell base 31 and has an entrance plane 21a, 22a and an exit plane 21b, 22b that is not parallel to the entrance plane 21a, 22a; and a lens drive mechanism 25 that can rotate the lens 21, 22 for adjusting the optical axis so that the angle at which the parallel light beam enters into the entrance plane 21a, 22b can be changed, wherein a detecting surface 52b for adjusting the optical axis is formed on a photodetector 52.

3 Claims, 6 Drawing Sheets refractive index: 1.46 refractive index: 1.51

PARTICLE SIZE DISTRIBUTION MEASURING APPARATUS

BACKGROUND OF THE INVENTION

1. Field of the Invention

The present invention relates to a particle size distribution measuring apparatus for measuring the distribution of particle size in a group of particles to be measured included in an object to be measured using an optical technique (for example, a laser diffraction/scattering means).

2. Description of Related Art

In laser diffraction/scattering-type particle size distribution measuring apparatuses, a group of particles to be measured (for example, a powder) in a dispersed state in a medium (for example, water or air) is irradiated with a parallel light beam so that the spatial distribution of the light intensity of the scattered light that has been diffracted/scattered by the group of particles to be measured can be detected by a number of photodetector elements and, thus, an arithmetic operation is carried out using this distribution of the light intensity on the basis of the Fraunhofer diffraction theory and the Mie scattering theory so as to calculate the distribution of particle size of the group of particles to be measured.

FIG. 5 is a schematic diagram showing an example of the structure of a conventional particle size distribution measuring apparatus. FIG. 5 is a combination of a schematic diagram showing the structure of an optical system and a block diagram showing the structure of a data sampling circuit and a signal processing system utilizing a computer. In addition, the direction of a line connecting a light source unit to a ring detector (photodetector) is the X direction, one direction perpendicular to the X direction is the Y direction, and the direction perpendicular to the X and Y directions is the Z direction.

A particle size distribution measuring apparatus 101 is provided with a cell base 31 on which a cell 30 containing an object to be measured S (mixture of a liquid medium L and a group of particles to be measured P) is placed, a light source unit 40 for irradiating the cell 30 with a parallel light beam, a condensing lens 51, a ring detector 52 for detecting the distribution of the light intensity, a data sampling circuit 60, and a computer (control unit) 170 for controlling the entire particle size distribution measuring apparatus 101.

The light source unit 40 is installed in the left side portion of the particle size distribution measuring apparatus 101 and, typically, a laser light source 41, a condensing lens 42, a space filter 43, and a collimator 44 are provided in this order starting from the left.

In this structure of the light source unit 40, a laser beam generated by the laser light source 41 passes through the condensing lens 42, the space filter 43 and the collimator 44 so as to become a parallel light beam, which is then directed in the frontal direction (X direction, from left to right in the figure) in order to irradiate the cell 30.

As a result, the parallel light beam is diffracted/scattered by the group of particles to be measured P within the cell 30 so as to provide a spatial distribution pattern of the light intensity of the diffracted/scattered light when an object to be measured S is contained inside of the cell 30 that has been placed on the cell base 31.

Meanwhile, a condensing lens 51 and a ring detector 52 are provided in the right side portion of the particle size distribution measuring apparatus 101 in this order starting from the left.

The ring detector 52 is made up of a number of (for example, 64) photodetector elements (photodiodes) having detecting surfaces in a ring or a semi-ring form of which the radii differ from each other, which are positioned in concentric circles with the optical axis of the condensing lens 51 at the center. Each photodetector element allows light to enter therein at a diffracted/scattered angle corresponding to the position thereof. Accordingly, the output signal of each photodetector element indicates the intensity of light at each diffracted/scattered angle.

In this structure of the condensing lens 51 and ring detector 52, the diffracted/scattered light is condensed on a detecting surface of the ring detector 52 through the condensing lens 51 so as to form a diffraction/scattering image in a ring form.

Thus, the output signal of the ring detector 52 is sequentially digitalized by the data sampling circuit 60 made up of an amplifier, a multiplexer and an A-D convertor so as to be transmitted to the multipurpose computer 170 as the data of the light intensity distribution of the diffracted/scattered light.

The computer 170 is provided with a CPU 180 and a memory 190, and a display unit 71 having a monitor screen and an input apparatus 72 having a keyboard 72a and a mouse 72b are linked to the computer 170. When the functions are divided into blocks based on the processing of the CPU 180, the CPU 180 has an object measuring unit 81 for measuring an object to be measured S and a calculation unit 83 for calculating the distribution of particle size of the group of particles to be measured P. In addition, the memory 190 has a light intensity distribution storage region 91 for storing the data of light intensity distribution and a basic data storage region 92 for storing the refractive indices of particles and water (liquid medium L), publicly known equations for arithmetic operations on the basis of the Fraunhofer diffraction theory and the Mie scattering theory, and the like.

When a user inputs an instruction to measure an object to be measured S to the input apparatus 72, the object measuring unit 81 controls the system in such a manner that the cell 30 that contains the object to be measured S is irradiated with a parallel light beam from the light source unit 40 and the light intensity data from the ring detector 52, that is to say, the data of light intensity distribution is acquired so as to be stored in the light intensity distribution storage region 91.

The calculation unit 83 uses the data of light intensity distribution that has been acquired by measuring the object to be measured S and the refractive indices of the particles and the liquid medium L so as to carry out a publicly known arithmetic operation on the basis of the Fraunhofer diffraction theory and the Mie scattering theory and, thus, controls the system so that the particle size distribution of the group of particles to be measured P included in the object to be measured S can be calculated.

In this particle size distribution measuring apparatus 101, the optical axis of the condensing lens 51 and the center axis (optical axis) of the ring detector 52 must be along the same line with a high precision. However, the optical axis of the condensing lens 51 and the center axis of the ring detector 52 may not align with each other and, therefore, the optical axis of the condensing lens 51 and the center axis of the ring detector 52 are adjusted relative to each other for each measurement.

In order to do so, a detecting surface for adjusting the optical axis is formed in the center portion of the ring detector 52. FIG. 6 is a diagram showing an example of the ring detector 52. In the ring detector 52 a number of (for example, 5) photodetector elements 52a having detecting surfaces in a semi-ring form with radii that differ from each other are placed in concentric circles, with a circular detecting surface 52b for adjusting the optical axis at the center. The detecting surface 52b for adjusting the optical axis is divided into two in the Y direction and, at the same time, divided into two in the Z direction so as to be made up of four photodetector elements 52b'.

As a result, the ring detector 52 is shifted in the YZ directions by means of a drive mechanism (see FIG. 5) so that the intensity of the output signal that is outputted from each of the four photodetector elements 52b' becomes equal and, thus, the optical axes are matched prior to measurement.

Another type of particle size distribution measuring apparatus has also been developed wherein an auto-alignment mechanism is provided with an actuator for shifting the collimator 44 in the direction perpendicular to the optical axis instead of shifting the ring detector 52 in the YZ directions and an optical axis adjustment processing unit for feeding a control signal for shifting the collimator 44 to the actuator on the basis of the output signal from the detecting surface for adjusting the optical axis (see Patent Document 1).

PRIOR ART DOCUMENT

Patent Document

Patent Document 1: Japanese Unexamined Patent Publication H11(1999)-83721

SUMMARY OF THE INVENTION

1. Problem to Be Solved by the Invention

In the above described particle size distribution measuring apparatus 101, an actuator such as a piezoelectric element or a stepping motor is used as the drive mechanism 125 for shifting the ring detector 52 and, in this case, the amount of shift needs to be on the order of micrometers. Accordingly, such an actuator is complex and expensive.

In the particle size distribution measuring apparatus 101 having a condensing lens 51, the light that progresses at a predetermined angle forms an image in a predetermined location on the ring detector 52 after having passed through the condensing lens 51. Therefore, the direction in which light progresses is simply translated without any change in angle (direction) however the collimator 44 is shifted. Thus, the image is not formed at the center of the ring detector 52 in the case wherein the initial direction in which the light progresses is not directed towards the center of the ring detector 52.

2. Means for Solving Problem

The present applicant examined a method for allowing a parallel light beam from the light source unit 40 to form an image at the center of the ring detector 52 without the use of an actuator for adjusting the amount of shift by an order of micrometers. First, it was determined that the angle at which the parallel light beam from the light source unit 40 progresses (see FIG. 3) had to be adjusted. In this case also, however, it was necessary to rotate the light source unit 40 by an order of micrometers, which ended up requiring an actuator that is complex and expensive. Therefore, it was determined to use a lens of which the angle between the entrance plane and the exit plane had an inclination of 1° in order to adjust the angle at which the parallel light beam from the light source unit 40 progresses.

FIG. 4(a) is a graph showing the relationship between the angle α1 of a normal to an entrance plane relative to the direction in which the light enters and the angle α2 at which the light exits. This shows the results of the calculation when the refractive index of the lens is 1.46, the refractive index of the periphery of the lens is 1.0 and the angle of lens is 1 degree. Even when the angle α1 of the normal to the entrance plane relative to the direction in which light enters changes greatly, the angle α2 at which light exits does not change a great deal. In the case wherein the angle α1 of the normal to the entrance plane changes by 10° from 30° to 40°, for example, the angle α2 at which light exits only changes by 0.12°, which is approximately 1/100 of the change in the angle α1.

As a result, a lens for adjusting the optical axis having an entrance plane and an exit plane that is not parallel to the entrance plane can be provided so that the lens for adjusting the optical axis can be rotated by a large angle α1 by means of an inexpensive drive mechanism. Thus, it was found that the parallel light beam from the light source unit can focus an image at the center of the photodetector by shifting the direction in which light exits by a microscopic angle α2.

That is to say, the particle size distribution measuring apparatus according to the present invention is provided with: a light source unit for emitting a parallel light beam; a condensing lens for condensing scattered; a photodetector for detecting the distribution of light intensity of the scattered light that has been condensed by the above-described condensing lens; a cell base, on which a cell that contains an object to be measured including a group of particles to be measured is placed, located between the above-described light source unit and the above-described condensing lens; and a control unit for calculating the distribution of particle size of the group of particles to be measured included in the above-described object to be measured by allowing the above-described photodetector to detect the scattered light generated by irradiating the above-described object to be measured with a parallel light beam from the above-described light source unit after being condensed by the above-described condensing lens, wherein a detecting surface for adjusting the optical axis is formed on the above-described photodetector, and the particle size distribution measuring apparatus is further provided with: a lens for adjusting the optical axis which is placed between the above-described light source unit and the above-described cell base unit and which has an entrance plane through which a parallel light beam from the above-described light source unit enters and an exit plane that is not parallel to the entrance plane; and a lens drive mechanism that can rotate the above-described lens for adjusting the optical axis so that the angle at which a parallel light beam from the above-described light source unit enters into the above-described entrance plane can be changed.

3. Effects of the Invention

As described above, in the particle size distribution measuring apparatus according to the present invention, a parallel light beam from the light source unit can form an image at the center of the photodetector without the use of an actuator for adjusting the amount of shift by an order of micrometers.

4. Other Means for Solving Problem and Effects Thereof

In addition, in the particle size distribution measuring apparatus according to the present invention, the detecting surface of the above-described photodetector is placed parallel to the YZ plane in the case wherein the direction along a line connecting the above-described light source unit to the above-described photo detector is the X direction, one direction perpendicular the X direction is the Y direction, and the direction perpendicular to the X and Y directions is the Z direction, the above-described lens for adjusting the optical axis comprises a first lens of which the angle between the entrance plane and the exit plane is a first predetermined angle as viewed from the Y direction and a second lens of which the angle between the entrance plane and the exit plane is a second predetermined angle as viewed from the Z direction, and the above-described lens drive mechanism may make it possible for the above-described first lens to be rotated around an axis in the Y direction and for the above-described second lens to be rotated around an axis in the Z direction.

Here, the first and the second predetermined angles are any angles that have been determined in advance by the designer and are 0.2 degrees or greater or 5 degrees or less taking into consideration the relationship between the angle $\alpha 1$ of a normal to the entrance plane relative to the direction in which light enters and the angle $\alpha 2$ at which light exits.

In the particle size distribution measuring apparatus according to the present invention, the parallel light beam from the light source unit can form an image at the center of the photodetector even in the case wherein the parallel light beam from the light source unit has shifted in both the Y and Z directions.

Furthermore, in the particle size distribution measuring apparatus according to the present invention, the above-described detecting surface for adjusting the optical axis may be divided into two detecting surfaces in the Y direction and may also be divided into two detecting surfaces in the Z direction.

Moreover, in the particle size distribution measuring apparatus according to the present invention, the above-described control unit may output a drive signal to the above-described lens drive mechanism on the basis of the distribution of light intensity that has been detected on the above-described detecting surface for adjusting the optical axis before a cell has been placed on the above-described cell base.

In the particle size distribution measuring apparatus according to the present invention, the lens for adjusting the optical axis can be rotated by a large angle $\alpha 1$ by means of a lens drive mechanism so that the direction in which light exits can be shifted by a microscopic angle $\alpha 2$ and, therefore, it is not necessary to adjust the amount of shift by an order of micrometers. Thus, the control unit can allow a parallel light beam from the light source unit to focus an image at the center of the photodetector and, as a result, automation becomes possible.

DETAILED DESCRIPTION OF EMBODIMENTS

In the following, the embodiments of the present invention are described in reference to the drawings. The present invention is not limited to the embodiments as described below, and various modifications are included as long as the gist of the present invention is not deviated from.

Figure 1:
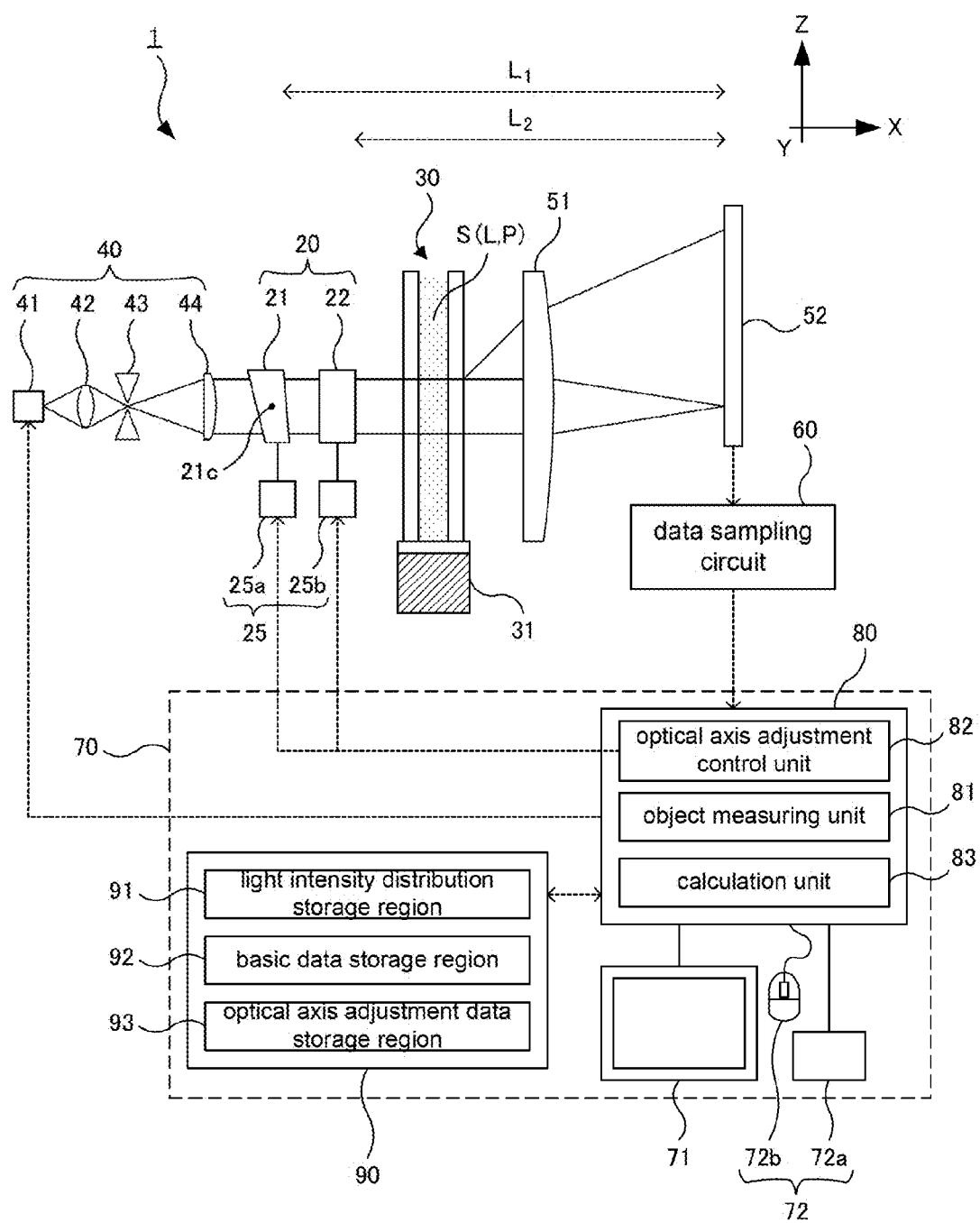
FIG. 1 is a schematic block diagram showing the entire structure of the particle size distribution measuring apparatus according to one embodiment of the present invention.
Figure 2:
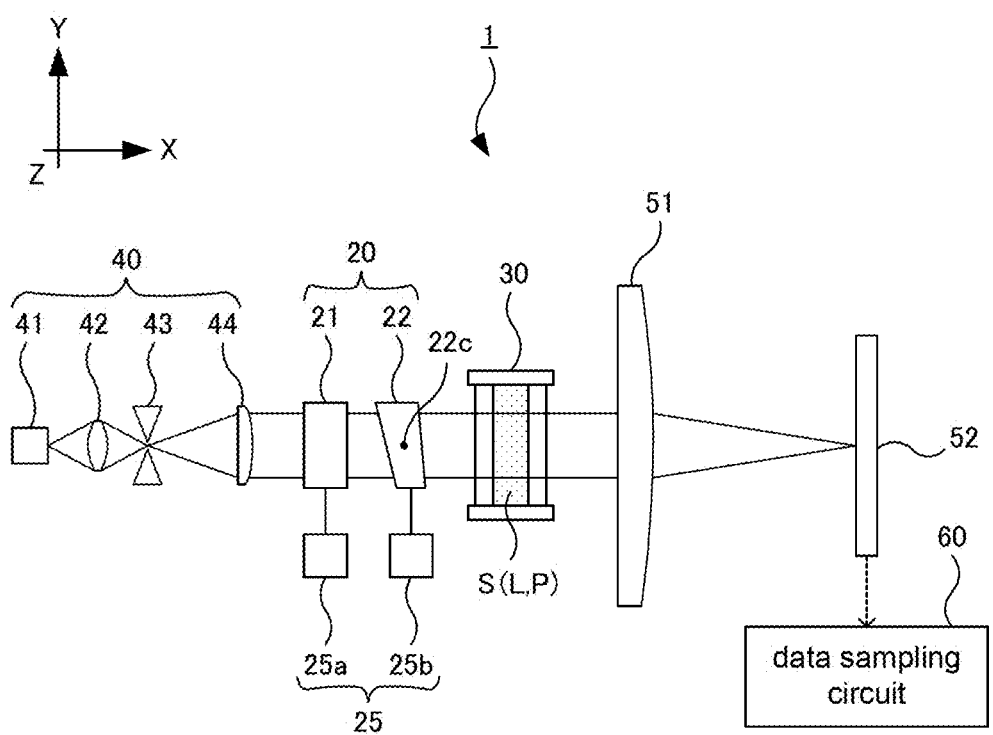
FIG. 2 is a diagram showing the particle size distribution measuring apparatus in FIG. 1 as viewed from a different direction (Z direction)

FIG. 1 is a schematic block diagram showing the entire structure of the particle size distribution measuring apparatus according to one embodiment of the present invention. FIG. 2 is a diagram showing the particle size distribution measuring apparatus in FIG. 1 as viewed from a different direction (Z direction). Here, FIG. 2 is merely a schematic diagram showing the structure of an optical system. In addition, the same symbols are attached to the same components as in the particle size distribution measuring apparatus 101.

The particle size distribution measuring apparatus 1 is provided with: a cell base 31 on which a cell 30 containing an object to be measured S (mixture of liquid medium L and a group of particles to be measured P); a light source unit 40 for irradiating the cell 30 with a parallel light beam; a lens 20 for adjusting the optical axis; a lens drive mechanism 25; a condensing lens 51; a ring detector 52 (photodetector) for detecting the distribution of light intensity; a data sampling circuit 60; and a computer 70 (control unit) for controlling the entire particle size distribution measuring apparatus 1.

The lens 20 for adjusting the optical axis is located between the light source unit 40 and the cell base 31 and is made up of a first glass lens 21 and a second glass lens 22 which are provided in this order from the left.

Figure 3A:
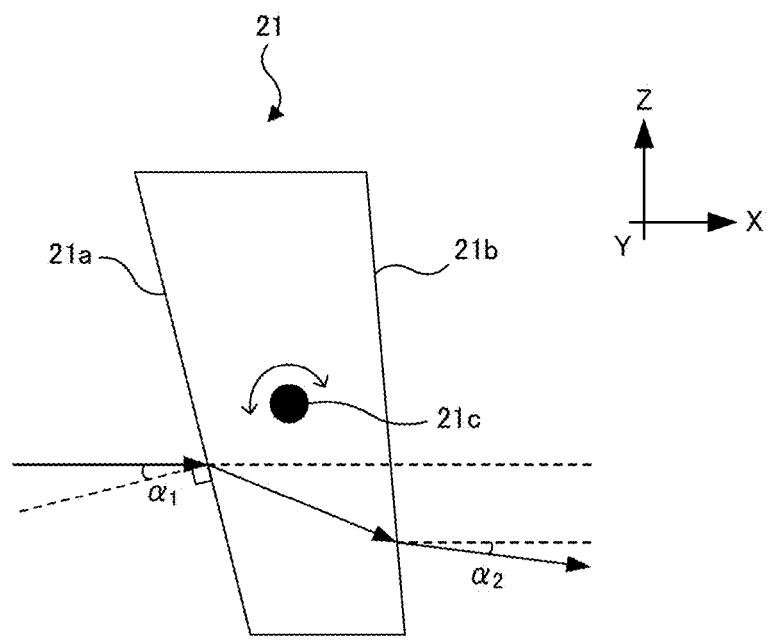
FIGS. 3(a) and 3(b) are diagrams showing an example of a first glass lens.
Figure 3B:
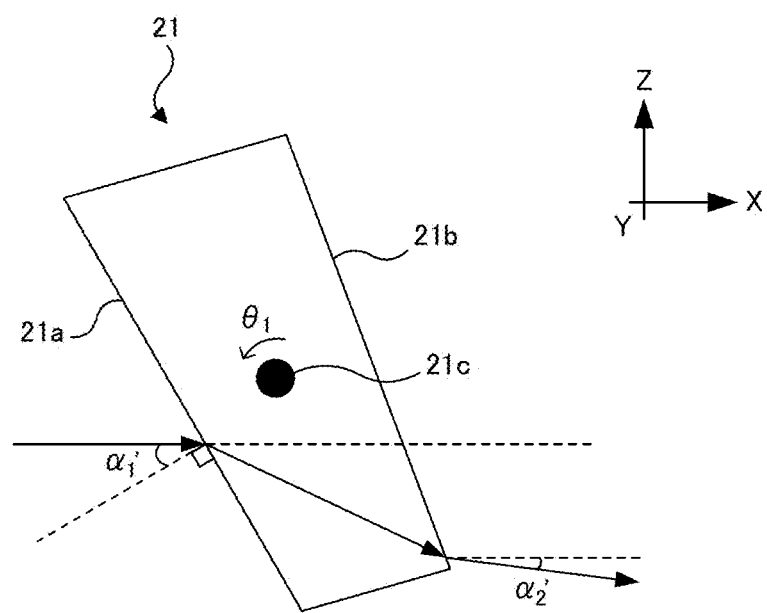

FIGS. 3(a) and 3(b) are diagrams showing an example of the first glass lens 21. Though the first glass lens 21 is in an approximately rectangular parallelepiped form, the surfaces facing each other in the direction along the optical axis of the laser beam are not parallel to each other but are inclined slightly relative to each other. That is to say, the angle between the entrance plane 21a on the light source unit 40 side and the exit plane 21b on the side opposite to the light source unit 40 is 1° (first predetermined angle) as viewed in the Y direction. Thus, the first glass lens 21 is provided in a location at a distance $L_1$ (for example, 400 mm) from the ring detector 52 (see FIG. 1) and is rotatable in the clockwise and counterclockwise directions around the axis of rotation 21c in the Y direction.

Here, the first glass lens 21 is made of crystal glass of which the refractive index is approximately 1.46, for example. In addition, the first glass lens 21 may be made of borosilicate glass (BK7). The refractive index of borosilicate glass is approximately 1.51.

Figure 4A:
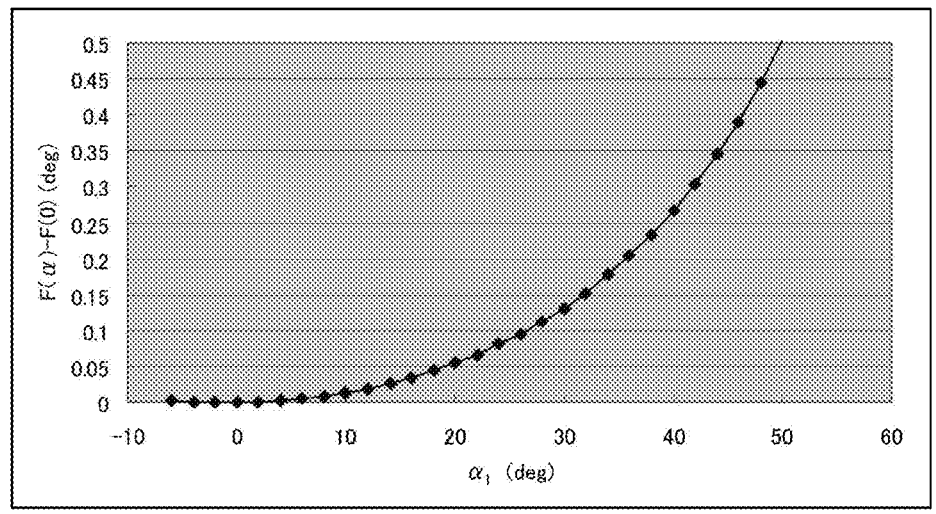
FIGS. 4(a) and 4(b) are graphs showing the relationships between the angle $\alpha 1$ of a normal to an entrance plane relative to the direction in which light enters and the angle $\alpha 2$ at which light exits.
Figure 4B:
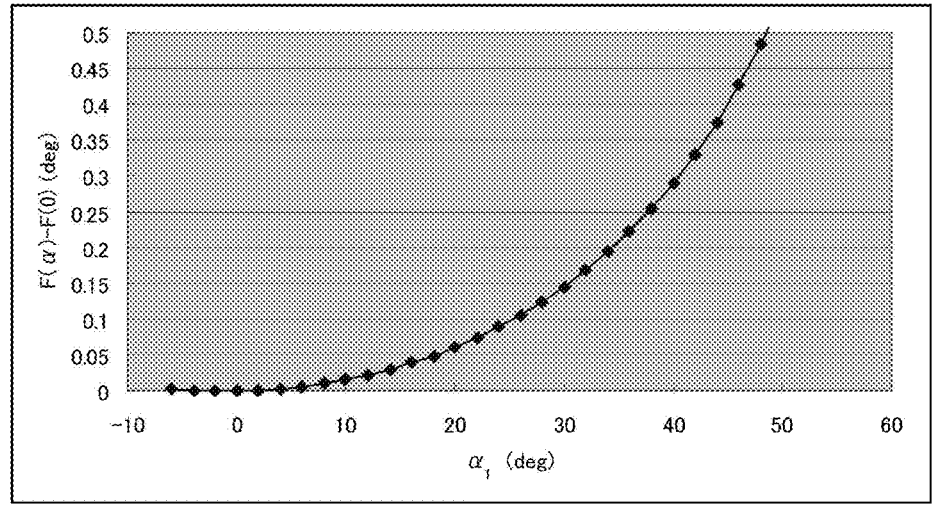
Figure 5:
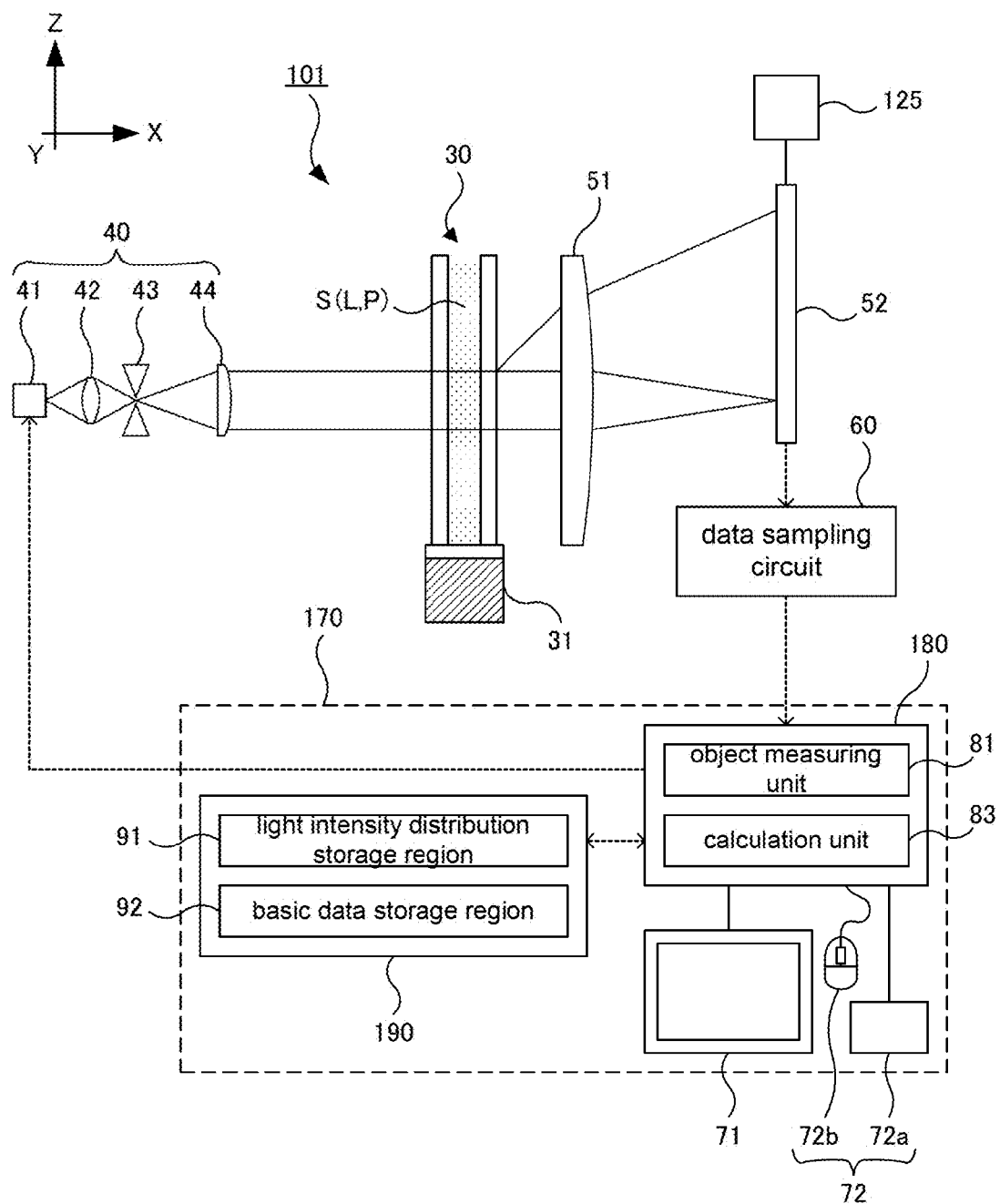
FIG. 5 is a schematic diagram showing an example of the structure of a conventional particle size distribution measuring apparatus.
Figure 6:
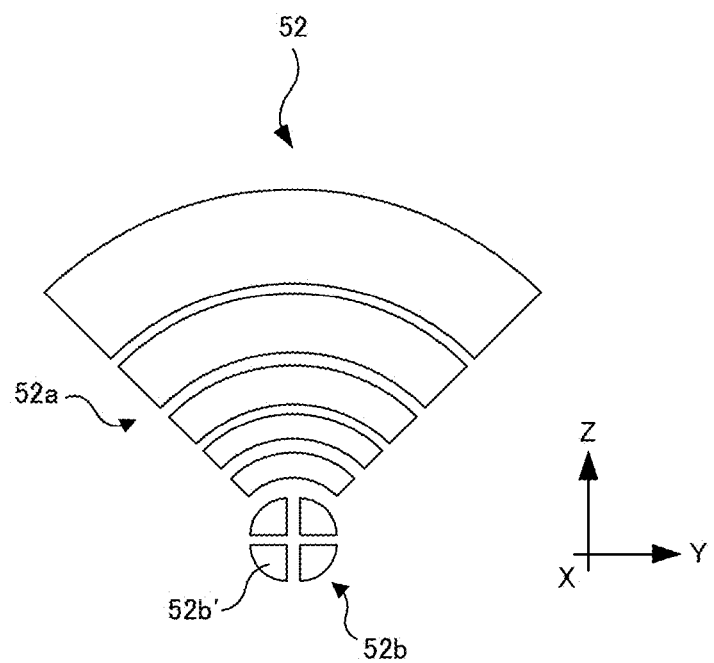
FIG. 6 is a diagram showing an example of a ring detector.

FIGS. 4(a) and 4(b) are graphs showing the relationship between the angle $\alpha_1$ of a normal to the entrance plane relative to the direction in which light enters and the angle $\alpha_2$ at which light exits. FIG. 4(a) shows a case wherein the lens is made of crystal glass and, thus, shows the results of calculation when the refractive index of the lens is 1.46, the refractive index of the periphery of the lens is 1.0 and the angle of the lens is 1 degree. In addition, FIG. 4(b) shows a case wherein the lens is made of borosilicate glass (BK7) and, thus, shows the results of calculation when the refractive index of the lens is 1.51, the refractive index of the periphery of the lens is 1.0 and the angle of the lens is 1 degree.

It can be seen from the graphs that when the first glass lens 21 rotates by a predetermined angle $\theta_1$, the angle $\alpha_1$ of a normal to the entrance plane 21a of the first glass lens 21 relative to the parallel light beam from the light source unit 40 changes as viewed in the Y direction and, at the same time, the angle ($\alpha_1$−1°) of the exit plane 21b of the first glass lens 21 also changes. In the case wherein the angle $\alpha_1'$ of the normal to the entrance plane 21a relative to the parallel light beam from the light source unit 40 changes by 10° from 30° to 40°, for example, the angle $\alpha_2'$ at which light exits from the exit plane 21b changes by 0.12° in the Z direction (see FIGS. 4(a) and 4(b)). That is to say, even in the case wherein the direction in which the parallel light beam is directed from the light source unit 40 shifts in the Z direction from the center of the ring detector 52 by a distance $K_z$ (described below), this can be corrected.

Here, it is preferable for the initial angle of the first glass lens 21 to be set such that the entrance plane 21a is inclined by an angle of 30°±10° relative to the X direction taking into consideration the relationship between the angle $\alpha_1$ of the normal to the entrance plane 21a relative to the direction in which light enters and the angle $\alpha_2$ at which light exits.

The second glass lens 22 is made of the same material and has the same form as the first glass lens 21. The angle between the entrance plane 22a on the light source unit 40 side and the exit plane 22b on the side opposite to the light source unit 40 is 1° (second predetermined angle) as viewed in the Z direction. In addition, the second glass lens 22 is provided in a location at a distance $L_2$ (for example, 350 mm) from the ring detector 52 and is rotatable in the clockwise and counterclockwise directions around the axis of rotation 21c in the Z direction.

It can be seen from the graphs that when the second glass lens 22 rotates by a predetermined angle $\theta_2$, the angle $\beta_1$ of a normal to the entrance plane 22a of the second glass lens 22 relative to the parallel light beam from the light source unit 40 changes as viewed in the Z direction and, at the same time, the angle ($\beta_1$−1°) of the exit plane 22b of the second glass lens 22 also changes. In the case wherein the angle $\beta_1$ of the normal to the entrance plane 22a relative to the parallel light beam from the light source unit 40 changes by 10° from 30° to 40°, for example, the angle $\beta_2$ at which light exits from the exit plane 22b changes by 0.12° in the Y direction (see FIGS. 4(a) and 4(b)). That is to say, even in the case wherein the direction in which the parallel light beam is directed from the light source unit 40 shifts in the Y direction from the center of the ring detector 52 by a distance $K_y$ (described below), this can be corrected.

Here, it is preferable for the initial angle of the second glass lens 22 to be set such that the entrance plane 22a is inclined by an angle of 30°±10° relative to the X direction taking into consideration the relationship between the angle $\beta_1$ of the normal to the entrance plane 22a relative to the direction in which light enters and the angle $\beta_2$ at which light exits.

The lens drive mechanism 25 is provided with an actuator 25a for rotating the first glass lens 21 around an axis 21c in the Y direction on the basis of a drive signal from the computer 70 and an actuator 25b for rotating the second glass lens 22 around an axis 22c in the Z direction. The actuator 25a and the actuator 25b may rotate the first glass lens 21 and the second glass lens 22, respectively, by a large angle of approximately ±10 degrees and, therefore, high precision control of a microscopic angle range, such as of ±1 degree or less, is not necessary. In other words, the rotational drive mechanism can be formed using a linear drive mechanism so that microscopic movement on an order of micrometers is not necessary and, thus, the cost can be reduced.

The computer 70 is provided with a CPU 80 and a memory 90, and a display unit 71 having a monitor screen and an input apparatus 72 having a keyboard 72a and a mouse 72b are linked to the computer 70. When the functions are divided into blocks based on the processing of the CPU 80, the CPU 80 has an object measuring unit 81 for measuring an object to be measured S, a calculation unit 83 for calculating the distribution of particle size of the group of particles to be measured P and an optical axis adjustment control unit 82. In addition, the memory 90 has a light intensity distribution storage region 91 for storing the data of light intensity distribution, a basic data storage region 92 for storing the refractive indices of particles and water (liquid medium L), publicly known equations for arithmetic operations on the basis of the Fraunhofer diffraction theory and the Mie scattering theory, and the like, and an optical axis adjustment data storage region 93.

The optical axis adjustment data storage region 93 stores in advance a first correspondence table showing the relationship between the angle $\alpha_2$ at which light exits from the exit plane 21b of the first glass lens 21 and the rotational angle $\theta_1$ of the first glass lens 21 and a second correspondence table showing the relationship between the angle $\beta_2$ at which light exits from the exit plane 22b of the second glass lens 22 and the rotational angle $\theta_2$ of the second glass lens 22.

When a user inputs an instruction to adjust the optical axis to the input apparatus 72, the optical axis adjustment control unit 82 allows the light source unit 40 to emit a parallel light beam and acquires data of light intensity, that is to say, four output signals from the detecting surface 52b for adjusting the optical axis of the ring detector 52 and, thus, controls the system so that a drive signal is outputted to the lens drive mechanism 25 on the basis of the first and second correspondence tables.

In the case wherein it is determined on the basis of the four output signals that the optical axis has shifted from the center axis of the ring detector 52 by a distance $K_y$ in the Y direction and by a distance $K_z$ in the Z direction, first, the distance $K_y$ and the distance $L_2$ between the second glass lens 22 and the ring detector 52 are used to calculate the angle by which the angle $\beta_2$ at which light exits from the exit plane 22b of the second glass lens 22 should be changed. Then, the angle $\theta_2$ by which the second glass lens 22 is changed is calculated on the basis of the second correspondence table and a drive signal is outputted to the actuator 25b.

Next, the distance $K_z$ and the distance $L_1$ between the first glass lens 21 and the ring detector 52 are used to calculate the angle by which the angle $\alpha_2$ at which light exits from the exit plane 21b of the first glass lens 21 should be changed. Then, the angle $\theta_1$ by which the first glass lens 21 is changed is calculated on the basis of the first correspondence table and a drive signal is outputted to the actuator 25a.

As described above, in the particle size distribution measuring apparatus 1, a parallel light beam from the light source unit 40 can form an image at the center of the ring detector 52 without the use of an actuator for adjusting the amount of shift by an order of micrometers. Furthermore, the direction in which light exits can be shifted by microscopic angles $\alpha_2$ and $\beta_2$ when the actuators 25*a* and 25*b* rotate the first glass lens 21 and the second glass lens 22 by large angles $\theta_1$ and $\theta_2$, respectively. Therefore, it is not necessary to adjust the amount of shift on an order of micrometers and, thus, the optical axis adjustment control unit 82 can allow a parallel light beam from the light source unit 40 to form an image at the center of the ring detector 52 and, as a result, automation is made possible.

Other Embodiments (1) Though the above described particle size distribution measuring apparatus 1 has such a structure that the optical axis adjustment control unit 82 outputs a drive signal to the lens drive mechanism 25, the structure may be such that a user uses the input apparatus 72 in order to output a drive signal to the lens drive mechanism 25.

(2) Though the above described particle size distribution measuring apparatus 1 has such a structure that the first glass lens 21 and the second glass lens 22 of which the refractive index is approximately 1.46 are used, the structure may use first and second lenses made of materials of which the refractive indices are approximately from 1.3 to 1.6.

INDUSTRIAL APPLICABILITY

The present invention can be applied to particle size distribution measuring apparatuses for measuring the distribution of particle size of a group of particles to be measured included in an object to be measured in accordance with an optical technique.

EXPLANATION OF SYMBOLS

1 particle size distribution measuring apparatus
21 first glass lens (lens for adjusting optical axis)
22 second glass lens (lens for adjusting optical axis)
21*a*, 22*a* entrance plane
21*b*, 22*b* exit plane
25 lens drive mechanism
30 cell
31 cell base
40 light source unit
51 condensing lens
52 ring detector (photodetector)
52*b* detecting surface for adjusting the optical axis
70 control unit

What is claimed is:

1. A particle size distribution measuring apparatus, comprising:
 a light source unit for emitting a parallel light beam;
 a condensing lens for condensing scattered;
 a photodetector for detecting the distribution of light intensity of the scattered light that has been condensed by said condensing lens;
 a cell base, on which a cell that contains an object to be measured including a group of particles to be measured is placed, located between said light source unit and said condensing lens; and
 a control unit for calculating the distribution of particle size of the group of particles to be measured included in said object to be measured by allowing said photodetector to detect the scattered light generated by irradiating said object to be measured with a parallel light beam from said light source unit after being condensed by said condensing lens, characterized in that
 a detecting surface for adjusting the optical axis is formed on said photodetector, and
 wherein the particle size distribution measuring apparatus further comprises:
 a lens for adjusting the optical axis which is placed between said light source unit and said cell base unit and which has an entrance plane through which a parallel light beam from said light source unit enters and an exit plane that is not parallel to the entrance plane; and
  a lens drive mechanism that can rotate said lens for adjusting the optical axis so that the angle at which a parallel light beam from said light source unit enters into said entrance plane can be changed; and
 wherein the detecting surface of said photodetector is placed parallel to the YZ plane in the case wherein the direction along a line connecting said light source unit to said photo detector is the X direction, one direction perpendicular the X direction is the Y direction, and the direction perpendicular to the X and Y directions is the Z direction,
 wherein said lens for adjusting the optical axis comprises a first lens of which the angle between the entrance plane and the exit plane is a first predetermined angle as viewed from the Y direction and a second lens of which the angle between the entrance plane and the exit plane is a second predetermined angle as viewed from the Z direction, and
 wherein said lens drive mechanism makes it possible for said first lens to be rotated around an axis in the Y direction and for said second lens to be rotated around an axis in the Z direction.

2. The particle size distribution measuring apparatus according to claim 1, characterized in that said detecting surface for adjusting the optical axis is divided into two detecting surfaces in the Y direction and is also divided into two detecting surfaces in the Z direction.

3. The particle size distribution measuring apparatus according to claim 2, characterized in that said control unit outputs a drive signal to said lens drive mechanism on the basis of the distribution of light intensity that has been detected on said detecting surface for adjusting the optical axis before a cell has been placed on said cell base.

* * * * *